(12) United States Patent
Chen

(10) Patent No.: US 8,158,141 B2
(45) Date of Patent: Apr. 17, 2012

(54) CELL TRANSPLANT DEVICE FOR TREATMENT OF CORNEAL WOUND

(76) Inventor: Paul Hong-Dze Chen, Rancho Santa Fe, CA (US)

( * ) Notice: Subject to any disclaimer, the term of this patent is extended or adjusted under 35 U.S.C. 154(b) by 1690 days.

(21) Appl. No.: 11/270,942

(22) Filed: Nov. 9, 2005

(65) Prior Publication Data

US 2007/0106394 A1     May 10, 2007

(51) Int. Cl.
*A61F 2/00* (2006.01)
*C12N 11/02* (2006.01)
*C12N 11/10* (2006.01)
*C12N 11/08* (2006.01)
*C12N 5/07* (2010.01)
*C12M 1/00* (2006.01)

(52) U.S. Cl. ........ 424/423; 435/177; 435/178; 435/180; 435/395; 435/283.1

(58) Field of Classification Search .................. None
See application file for complete search history.

(56) References Cited

U.S. PATENT DOCUMENTS

| | | | |
|---|---|---|---|
| 4,744,362 A * | 5/1988 | Grundler ...................... 606/166 |
| 4,983,181 A | 1/1991 | Civerchia | |
| 4,994,081 A | 2/1991 | Civerchia et al. | |
| 5,000,963 A | 3/1991 | Hefton | |
| 5,030,230 A * | 7/1991 | White ......................... 623/5.14 |
| 5,112,350 A | 5/1992 | Civerchia et al. | |
| 5,489,304 A | 2/1996 | Orgill et al. | |
| 5,522,888 A | 6/1996 | Civerchia | |
| 5,643,187 A | 7/1997 | Næstoft et al. | |
| 5,654,135 A | 8/1997 | Tinois et al. | |
| 5,693,332 A | 12/1997 | Hansbrough | |
| 5,712,137 A | 1/1998 | Barlow et al. | |
| 5,716,411 A | 2/1998 | Orgill et al. | |
| 5,716,633 A | 2/1998 | Civerchia | |
| 6,039,972 A | 3/2000 | Barlow et al. | |
| 6,093,868 A | 7/2000 | Sawano et al. | |
| 6,187,053 B1 | 2/2001 | Minuth | |
| 6,274,787 B1 | 8/2001 | Downing | |
| 6,296,867 B1 | 10/2001 | Peyman | |
| 6,333,029 B1 | 12/2001 | Vyakarnam et al. | |
| 6,534,084 B1 | 3/2003 | Vyakarnam et al. | |
| 6,541,028 B1 | 4/2003 | Kuri-Harcuch et al. | |
| 6,793,677 B2 | 9/2004 | Ferree | |
| 6,821,107 B1 | 11/2004 | Hara et al. | |
| 6,880,558 B2 | 4/2005 | Perez | |
| 2003/0018347 A1 | 1/2003 | Pallikaris et al. | |

OTHER PUBLICATIONS

He YG, McCulley JP "Growing human corneal epithelium on collagen shield & subsequent transfer to denuded cornea in vitro" [abstract], CurrEyeRes. Sep. 1991;10(9):851-63, Texas(US).
McCulley JP, et al., "In vitro transfer of rabbit corneal epithelium from carriers to denuded corneas or cryolathed lenticules"[abstract], Cornea. Nov. 1991;10(6):466-77, Texas.
"Fibrin Sealant in Corneal Stem Cell Transplantation" [abstract], Ophthalmology Review, Jun. 28, 2005, Cornea. 24(5):593-598, Jul. 2005.
M Iwata, et al. "Intercellular adhesion molecule-1 expression on human corneal epithelial outgrowth from limbal explant in culture" British Jour.of Ophthalmology 2003;87:203-7.
Yu-Guang He et al., Growing Human Corneal Epithelium on Collagen Shield and Subsequent Transfer to Denuded Cornea In Vitro, *Current Eye Research*, vol. 10, No. 9, Oxford University Press (1991), 13 pages.

* cited by examiner

*Primary Examiner* — David Naff
(74) *Attorney, Agent, or Firm* — Knobbe Martens Olson & Bear LLP

(57) ABSTRACT

A device for transplanting a graft such as a layer or layers of cultivated, autologous, allogenic or xenogenic cells to cover an accidental or surgical wound. The graft is cultivated and carried on a bed of collagen or other dissolvable or releasable material mounted on a protective substrate molded to conform to the profile of the wounded area and provided with a lateral attachment zone. The device facilitates the graft cultured in vitro to the recipient surface.

7 Claims, 3 Drawing Sheets

CELL TRANSPLANT DEVICE FOR TREATMENT OF CORNEAL WOUND

FIELD OF THE INVENTION

The invention relates to the culturing of grafts and other healing tissues and to their transfer and anchoring, upon a wounded area.

BACKGROUND

A corrective eye surgery such as laser photo-refractive keratectomy requires the peeling away of the corneal epithelial layer before the underlying stroma tissue is selectively ablated; after which, the epithelial layer is either discarded or flipped back over the laser-corrected area.

In the course of the procedure, the epithelial layer is subject to be torn or crinkled to the point where the ablated area is not fully covered by epithelial cells and subject to contamination and uneven healing or the epithelial layer has been too mechanically traumatized to be viable.

Grafts of epithelial cells, dermis or epidermis are now routinely cultured and transferred upon burns and other wounded areas as disclosed in U.S. Pat. No. 6,541,028 which patent is incorporated in this Specification by this reference. The handling of the graft and its correct positioning over the wound requires great dexterity on the part of the surgeon in order to avoid damaging of the graft and improper coverage or the wound. Furthermore, movement of the graft on the wound after application often causes graft failure due to poor adhesion or mechanical movement and trauma.

The re-connection of severed nerves, tendons, blood vessels, and other filiform tissues is commonly enhanced by the use of scaffolding material such as a mesh sleeve into which the ends of the severed tissue can grow and reconnect. When dealing with very small filiform tissues such as nerves, the construction and handling of the scaffolding structure becomes extremely difficult due to the smallness of the severed tissue and the available work zone.

The instant invention results from an attempt to devise some structural implements that can facilitate the culturing, transfer and installation of grafts without compromising their integrity.

SUMMARY

The instant embodiments provide a carrier upon which a graft or healing tissue such as a monolayer or polylayer of cells can be cultured then transported and intimately and accurately positioned upon an accidental or surgical wound. The carrier is particularly useful in the culturing and grafting of a layer of cells to a mammalian subject whose cornea has been ablated in the course of a photo-refractive keratectomy operation after removal of the epithelial cover.

In one embodiment of the invention, the carrier is a molded structure in the shape of a dome of which a posterior, concave section is shaped and dimensioned to accurately match the profile of a human cornea. A layer of dissolvable collagen interposed between the molded substrate and the epithelial cells facilitates the release of the cell upon the accidentally wounded or surgically ablated cornea. A lateral portion of the substrate projects peripherally and is coated with an adhesive or is sutured to the corneal limbus or sclera.

The peripheral portion of the device that is used to secure it in place can be formed in the shape of an ophthalmic conformer bearing patches of ophthalmologically safe adhesive. The shape of an ophthalmic conformer helps minimize graft movement on the eye and facilitates cell adhesion and transfer.

In another embodiment of the invention, channels are cut into a posterior face of a slab of biocompatible material, and dimensioned and oriented to intimately nest a damaged nerve or other filiform tissue. The second slab of biocompatible material is shaped in a mirror image of the first one, and joined to it to form a pair of clamping shells that completely surround the damaged tissue. Fenestrations drilled between the channel and the anterior face of each slab provide tunnels through which branches of the nerve can grow.

Alternatively, in yet other embodiments cultured nerve cells can be grown in the channels and the ends of the damaged nerves can be attached to the edges of the device. The anterior fenestrated face of each slab can be placed over the target effector tissue such as a muscle group.

Other embodiments provide a live tissue transplant device which comprises: a substrate having an active posterior face and an opposite anterior face; said posterior face having a central active zone and a lateral attachment zone; said active zone comprising: a releasable support layer, and a layer of cells cultured upon said device and spread over said support layers; and said attachment zone comprising means for securing said substrate around a wound.

In some embodiments said substrate comprises a sheet of material. In some embodiments said attachment zone comprises a peripheral margin of said sheet. In some embodiments said means for securing comprise at least one patch of adhesive material applied to said peripheral margin. In some embodiments said substrate comprises a molded body shaped and dimensioned to conform to the profile of said tissue. In some embodiments said body defines a dome having a concave posterior face dimensioned to intimately mate with a section of a cornea. In some embodiments said body has a channel cut in said posterior face, said channel being dimensioned to receive a filiform tissue. In some embodiments said substrate comprises a slab of biocompatible material.

In some embodiments the device has fenestrations between said channel and said anterior face. In some embodiments a second device is provided which is shaped and dimensioned as a mirror image thereof, wherein said devices are joined about their posterior faces to form a tunnel around a filiform tissue. In some embodiments said channel is shaped and dimensioned to nest a nerve section. Yet other embodiments further comprise means for dissolving said support layer. In some embodiments said support layer is taken from a group consisting essentially of collagen, amnionic membrane, cellulose, gelatin, and agarose. In some embodiments said adhesive material is taken from a group consisting essentially of fibrin and cyanoacrylate.

In some embodiments the device further comprises at least one partition projecting from said posterior face and dividing said active zone into separate areas. In some embodiments said substrate is formed in the shape of an ophthalmic conformer. In some embodiments said substrate is formed in the shape of a contact lens. In some embodiments said substrate comprises adhesive patches astride said support layer. Some embodiments further comprise a peripheral skirt surrounding said support layer.

Still further embodiments provide a method, for culturing, transplanting and securing a graft over a surgically or accidentally wounded area, which comprises: procuring a first substrate having an outer face and an inner face, said inner face being shaped and dimensioned to conform to the shape of said area; coating a portion of said inner face with a sheet of releasable biocompatible material; culturing at least one layer of live tissue cells upon said sheet; applying said substrate sheet and layer to said area; and securing said substrate to said area.

In some embodiments releasable layer is taken from a group consisting essentially of collagen, amnionic membrane, cellulose, gelatin and agarose. In some embodiments said layer comprises epithelial cells, and said area consists of a cornea of a mammalian subject. In some embodiments said substrate is molded in the shape of a contact lens. In some embodiments said substrate is molded in the shape of an ophthalmic conformer. In some embodiments said substrate is molded in the shape of an adhesive skin bandage. In some embodiments said epithelial cells are autologous, allogenic or xenogenic to said subject. In some embodiments the method further comprises procuring a pair of said coated and layered substrates, one being a mirror image of the other, clamping said substrates together over a filiform tissue. In some embodiments said area consists of a cornea of mammalian subject and said layer comprises pumping cells selected from the group consisting of endothelial cells, kidney cells, gastric cells, intestinal cells and colon cells. In some embodiments said pumping cells are autologous, allogenic or xenogenic to said subject. In some embodiments said layer comprises stem cells. In some embodiments said stem cells are autologous, allogenic or xenogenic. In some embodiments said layer comprises cultured cartilage, bone, synovial, periostial, or marrow cells. In some embodiments said live tissue cells are autologous, allogenic or xenogenic. In some embodiments said layer comprises cultured neuron or glial cells, and said area comprises neural tissue of a mammalian subject. In some embodiments said live tissue cells are autologous, allogenic or xenogenic. In some embodiments said layer comprises epithelium, fibroblasts, or endothelium, and said area comprises skin of a mammalian subject. In some embodiments said live tissue cells are autologous, allogenic or xenogenic. In some embodiments said layer comprises smooth muscle cells, striated muscle cells, or cardiac muscle cells, and said area comprises muscle of a mammalian subject. In some embodiments said live tissue cells are autologous, allogenic or xenogenic. In some embodiments said layer comprises cardiac muscle cells, and said area comprises cardiac muscle of a mammalian subject. In some embodiments said cardiac muscle cells are autologous, allogenic or xenogenic.

DESCRIPTION OF THE PREFERRED EMBODIMENTS

Figure 1:
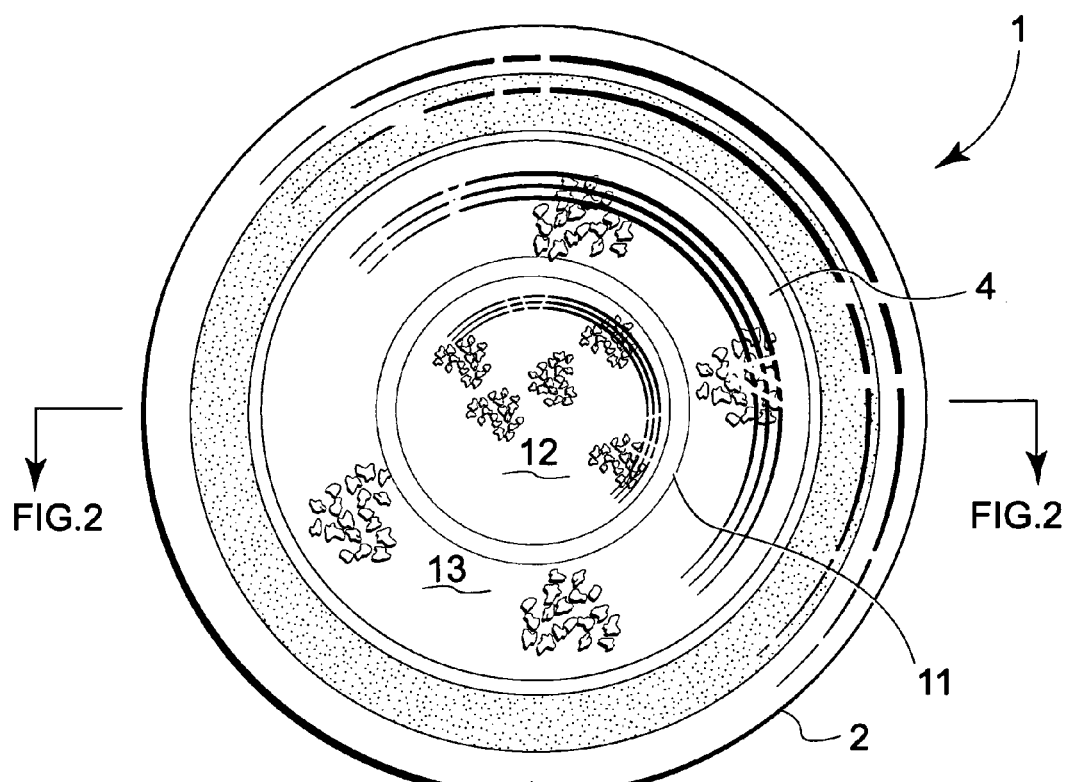
FIG. 1 is a diagrammatical plan view of the posterior face of a first embodiment of the invention.
Figure 2:
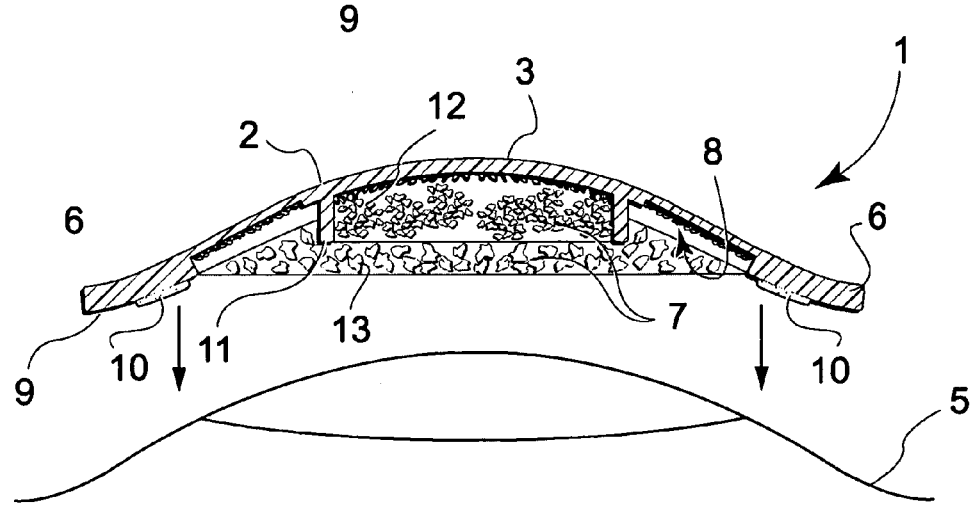
FIG. 2 is a cross-sectional view taken along line 2-2 of FIG. 1.

Referring now to the drawing, there is shown in FIGS. 1 and 2 live tissue culturing, transferring and installing device 1 according to the invention. The device comprises a molded, transparent substrate 2 shaped in the form of a dome 3 akin to a contact lens whose inner or posterior, concave face 4 is dimensioned to intimately mate with a surface section 5 of a mammalian cornea and sclera. Extending peripherally from the outer edge of the dome section 3 is lateral skirt portion forming a peripheral margin 6 which projects slightly posteriorly to contact the cornea or the sclera when the device is in place.

The substrate is preferably made of silicone, hydrogel, acrylate-hydrogel, silicone-acrylate, fluro-silicone acrylate or other ophthalmologically acceptable material known to those of ordinary skill in the art of contact lens manufacture.

In the process of a photo-refractive keratectomy operation, a central section of the corneal epithelial layer is completely removed before the corrective ablation of the underlying stromal tissue. One or more layers of cultured cells 7 are seeded upon a bed 8 of collagen coating the posterior or inner face 4 of the substrate. The bed or layer of collagen 8 is designed to facilitate the release of the epithelial cell upon the cornea 5. Other dissolvable or otherwise releasable biocompatible material may be used such as cellulose, gelatin, agarose, amnionic membrane, or other medium known to those with ordinary skill in the art, including such techniques in which the apical adhesion molecules of the epithelial cells in contact with the substrate can be released and the basal adhesion molecules in contact with the corneal stroma can be selectively released with the use of an antibiotic sensitive promoter. The posterior face 9 of the skirt 6 is preferably slightly textured to improve adhesion, and coated with a biocompatible glue 10 such as fibrin, cyano-acrylate, and other such ophthalmologically acceptable adhesive.

Optionally, one or more partitions 11 may project posteriorly from the substrate to separate diverse groups of culture cells. For example, the center section 12 may carry transparent epithelial cells to replace the removed section, while the peripheral annular section 13 may carry some healing culture such as stem cells, kidney cells, gastric cells, intestinal cells, colon cells, or corneal endothelial cells which pump fluid out of the cornea to maintain corneal clarity and minimize corneal edema.

The transparent substrate, collagen and cultured cells do not obstruct vision and provide an effective shield that prevents the cornea from touching debris or infective material.

Figure 3:
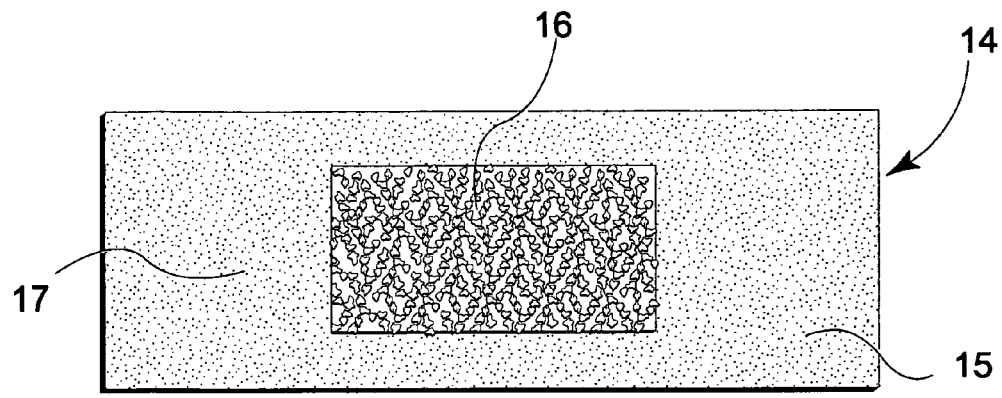
FIG. 3 is a diagrammatical plan view of the posterior face of a second embodiment of the invention.

FIG. 3 illustrates a first alternate embodiment 14 of the invention in which the substrate 15 is a pliable or rigid sheet of material carrying in its center a patch 16 of cultured cells over a bed of releasable material as previously described in connection with the first embodiment of the invention. The substrate may be made in the shape of a common adhesive skin bandage. Patches 17 of biocompatible glue facilitate the adhesion of the substrate to skin, muscles, bones or other tissues of which a damaged area is covered by the cultured layer 16. Alternatively, the slab may be made of a biocompatible porous foam material which may be placed on the surface of the body, or implanted within the body, in which it may be permanent or dissolvable.

Figure 4:
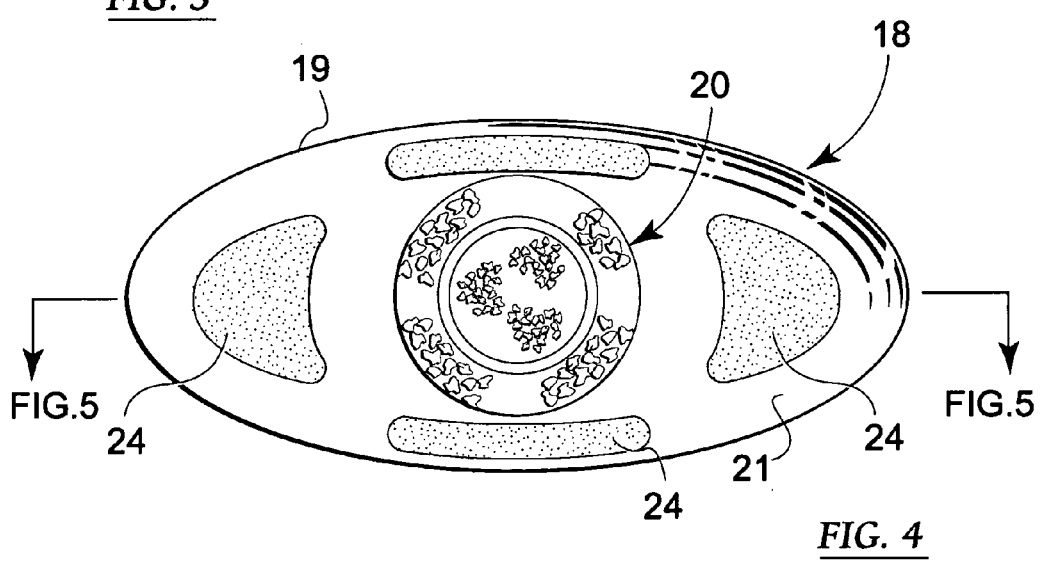
FIG. 4 is a diagrammatical plan view of the posterior face of a third embodiment of the invention.
Figure 5:
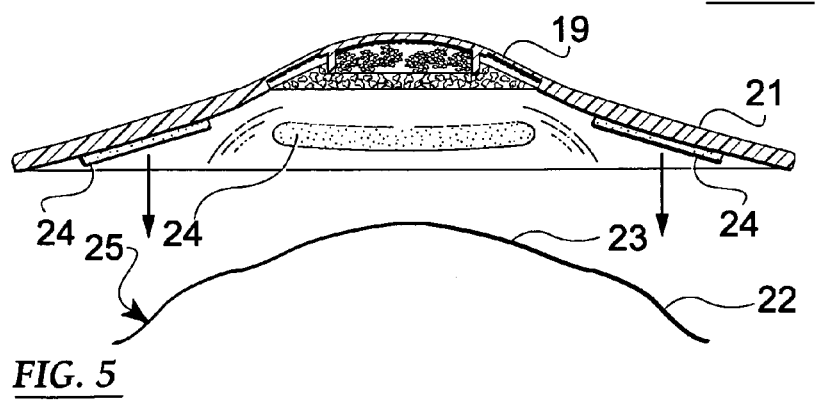
FIG. 5 is a cross sectional view taken along line 5-5 of FIG. 4.

FIGS. 4 and 5 illustrate a second alternate embodiment 18 of the invention in which the substrate 19 is formed in the shape of an ophthalmic conformer. The central portion of the device 20 is essentially similar to the one described in connection with the first embodiment of the invention. However, the peripheral skirt of the first embodiment is replaced here by a lateral projection 21 that extends peripherally to cover the sclera and limbus 22 of the cornea 23. Patches 24 of biocompatible glue are used to secure the device over the cornea. The shape of the ophthalmic conformer matches the shape of the eye socket and minimizes movements of the device, thus maximizing adhesion and transfer of the cells.

Figure 6:
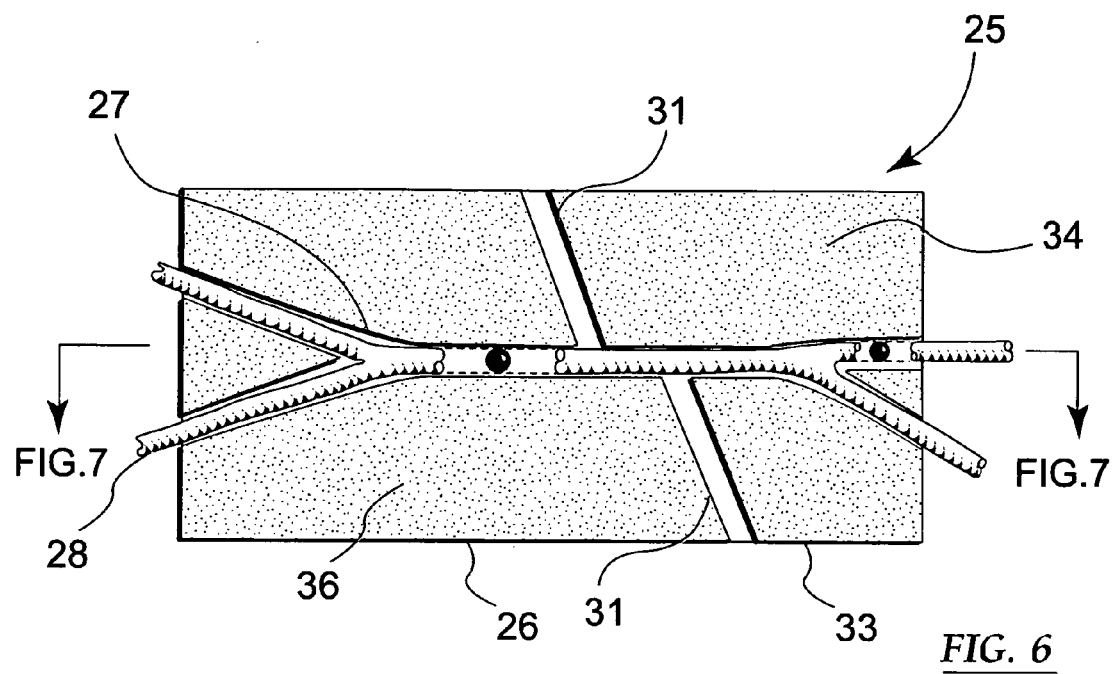
FIG. 6 is a diagrammatical plan view of the posterior face of a fourth embodiment of the invention.
Figure 7:
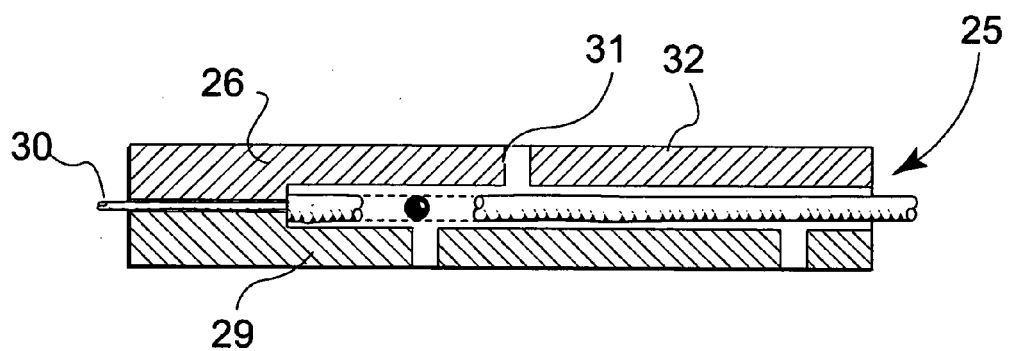
FIG. 7 is a diagrammatical cross-sectional view of a nerve healing device using mirror images of the fourth embodiment of the invention along line 7-7 of FIG. 6.

FIGS. 6 and 7 illustrate a third alternate embodiment of the invention particularly adapted to promote the healing of sections of filiform tissues such as a nerve, tendon, or blood vessel. The first slab 26 of polymer or other biocompatible material has a gutter or channel 27 carved into its posterior face 34. The channel 27 is shaped and dimensioned to conform to the shape of a nerve 28 or other filiform tissue. The channel is pre-seeded with cultured neurons and/or cultured glial cells. A second slab 29 of the same material as the first is shaped and dimensioned as a mirror image of the first slab 26 whereby the two slabs can be joined together about their posterior faces to form two clamping shells sandwiching the nerve section 28 therebetween. A layer of glue 30 is used to hold the two slabs together. Fenestration 31 between the channel 27 and the anterior face 32 and lateral faces 33 of the slabs form tunnels through which neurological branches can grow. Alternately, the slab may be made of a porous foam material which can serve as a scaffolding for the growth of filiform tissues.

Alternatively, cultured neuron and/or cultured glial cells can be grown in the channels, and the ends of the damaged nerves can be attached to the edges of the device with sutures or biocompatible glue. The anterior fenestrations can be placed over a target effector tissue such as a muscle group.

In each of the above-described embodiments, the cultured layer may comprise cultured stem cells to promote healing and regeneration.

While the preferred embodiments of the invention have been described, modifications can be made and other embodiments may be devised without departing from the spirit of the invention and the scope of the appended claims.

What is claimed is:

1. A living cell transplant device for treatment of a surgical or accidental corneal wound, wherein the device comprises:
   a) a removable substrate formed in the shape of a contact lens having a central zone and a lateral zone peripheral to the central zone, wherein the central zone comprises a concave posterior face and a convex anterior face, and wherein the substrate further comprises an ophthalmologically acceptable contact lens material;
   b) a releasable layer coating the concave posterior face;
   c) a plurality of living, transplantable cells upon the releasable layer, wherein the releasable layer is designed to facilitate release of the living, transplantable cells upon the corneal wound to effect transplantation thereof; and
   d) means for attaching the lateral zone of the substrate formed in the shape of a contact lens around the wound.

2. The device of claim 1, wherein the means for attaching the substrate in the form of a contact lens comprises at least one patch of adhesive material applied to the lateral zone.

3. The device of claim 1, which further comprises means for dissolving the releasable layer.

4. The device of claim 1, wherein the releasable layer is selected from the group consisting of collagen, amniotic membrane, cellulose, gelatin, and agarose.

5. The device of claim 2, wherein the adhesive material is selected from the group consisting of fibrin and cyanoacrylate.

6. The device of claim 1, which further comprises at least one partition projecting from the concave posterior face and dividing the central zone into separate areas.

7. The device of claim 1, wherein the contact lens is formed in the shape of an ophthalmic conformer.

* * * * *